(12) United States Patent
Burkett

(10) Patent No.: US 10,492,697 B2
(45) Date of Patent: *Dec. 3, 2019

(54) INTRAVASCULAR DEVICES, SYSTEMS, AND METHODS HAVING A CORE WIRE WITH EMBEDDED CONDUCTORS

(71) Applicant: VOLCANO CORPORATION, San Diego, CA (US)

(72) Inventor: David H Burkett, Panama City Beach, FL (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,704

(22) Filed: Apr. 5, 2018

(65) Prior Publication Data

US 2018/0220899 A1 Aug. 9, 2018

Related U.S. Application Data

(63) Continuation of application No. 14/611,921, filed on Feb. 2, 2015, now Pat. No. 9,955,878.

(Continued)

(51) Int. Cl.
*A61B 5/0215* (2006.01)
*A61B 5/00* (2006.01)
*A61B 18/14* (2006.01)
*A61B 5/026* (2006.01)
*A61B 5/01* (2006.01)
(Continued)

(52) U.S. Cl.
CPC .......... *A61B 5/0215* (2013.01); *A61B 5/6851* (2013.01); *A61B 18/1492* (2013.01); *A61B 5/01* (2013.01); *A61B 5/026* (2013.01); *A61B 8/12* (2013.01); *A61B 2018/0041* (2013.01); *A61B 2018/00386* (2013.01); *A61B 2018/00404* (2013.01); *A61B 2018/00577* (2013.01); *A61B 2018/1467* (2013.01); *A61B 2090/3735* (2016.02); *A61B 2090/3784* (2016.02); *A61B 2562/0247* (2013.01); *A61B 2562/227* (2013.01); *A61B 2562/228* (2013.01);
(Continued)

(58) Field of Classification Search
CPC .. A61B 5/0215; A61B 5/02152; A61B 5/6851
See application file for complete search history.

(56) References Cited

U.S. PATENT DOCUMENTS 5,125,137 A 6/1992 Corl
5,873,835 A 2/1999 Hastings
(Continued)

FOREIGN PATENT DOCUMENTS

EP 1897582 A1 3/2008
JP 2008062067 A 3/2008
(Continued)

*Primary Examiner* — Allen Porter

(57) ABSTRACT

Intravascular devices, systems, and methods are disclosed. In some instances, the intravascular device is a guide wire with electrical conductors embedded within a core wire. In some instances, the electrical conductors are coupled to conductive bands adjacent a proximal portion of the guide wire and a sensing element adjacent a distal portion of the guide wire. Methods of making, manufacturing, and/or assembling such intravascular devices and associated systems are also provided.

18 Claims, 3 Drawing Sheets

Related U.S. Application Data

(60) Provisional application No. 61/935,113, filed on Feb. 3, 2014.

(51) Int. Cl.
   *A61B 18/00* (2006.01)
   *A61B 90/00* (2016.01)
   *A61B 8/12* (2006.01)

(52) U.S. Cl.
   CPC ..... *A61M 2210/12* (2013.01); *A61M 2230/30* (2013.01); *Y10T 29/49171* (2015.01)

(56) References Cited

U.S. PATENT DOCUMENTS

| | | |
|---|---|---|
| 6,090,052 A | 7/2000 | Akerfeldt |
| 6,106,476 A | 8/2000 | Corl |
| 6,551,250 B2 | 4/2003 | Khalil |
| 7,930,014 B2 | 4/2011 | Huennekens |
| 2002/0151823 A1 | 10/2002 | Miyata et al. |
| 2003/0028128 A1 | 2/2003 | Tenerz |
| 2003/0139794 A1 | 7/2003 | Jenney |
| 2004/0116816 A1* | 6/2004 | Tenerz ............... A61B 5/02007 600/486 |
| 2006/0074318 A1 | 4/2006 | Ahmed |
| 2013/0261435 A1* | 10/2013 | Mellin ................. A61B 5/0215 600/424 |
| 2013/0274843 A1* | 10/2013 | Barker ................. A61N 1/0534 607/116 |
| 2014/0005543 A1 | 1/2014 | Burkett |
| 2014/0180141 A1 | 6/2014 | Millett |
| 2014/0187874 A1 | 7/2014 | Burkett |
| 2014/0187920 A1 | 7/2014 | Millett |
| 2014/0187980 A1 | 7/2014 | Burkett |
| 2014/0187984 A1 | 7/2014 | Burkett |
| 2015/0025330 A1 | 1/2015 | Davies |

FOREIGN PATENT DOCUMENTS

| | | |
|---|---|---|
| WO | 2009054805 A1 | 4/2009 |
| WO | 2011092190 A1 | 8/2011 |

* cited by examiner

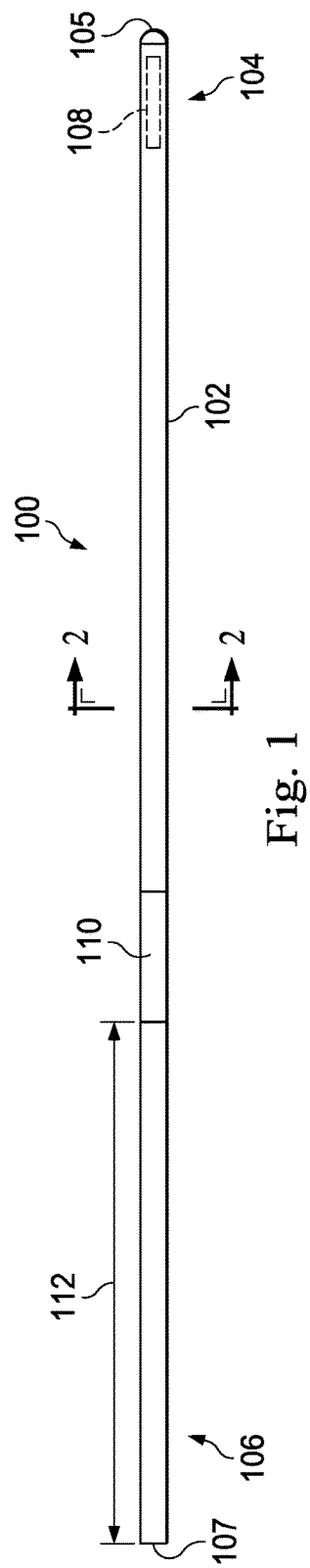
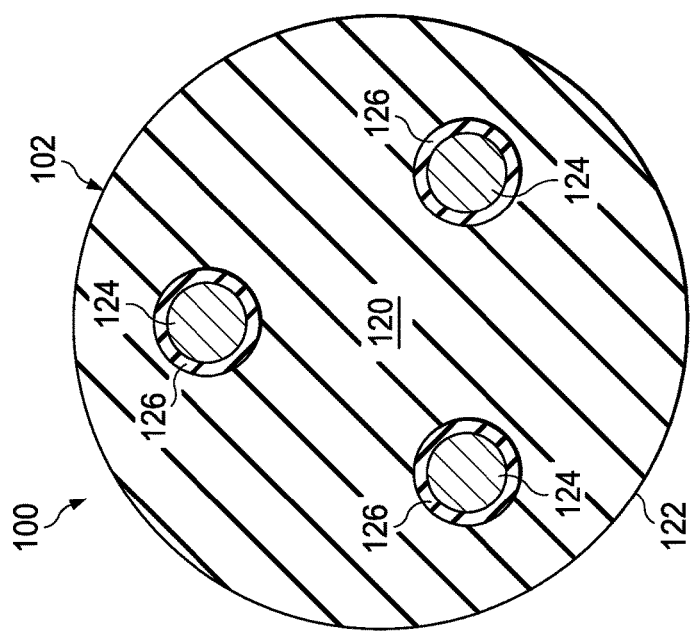

INTRAVASCULAR DEVICES, SYSTEMS, AND METHODS HAVING A CORE WIRE WITH EMBEDDED CONDUCTORS

CROSS REFERENCE TO RELATED APPLICATION

The present application is a continuation of U.S. patent application Ser. No. 14/611,921, filed Feb. 2, 2015, now U.S. Pat. No. 9,955,878, which claims priority to and the benefit of U.S. Provisional Patent Application No. 61/935,113 filed Feb. 3, 2014, each of which is hereby incorporated by reference herein in its entirety.

TECHNICAL FIELD

The present disclosure relates to intravascular devices, systems, and methods. In some embodiments, the intravascular devices are guide wires that include a core wire having one or more embedded conductors.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire. Further, due to its small diameter, in many instances the proximal connector portion of the guide wire (i.e., the connector(s) that facilitate communication between the electronic component(s) of the guide wire and an associated controller or processor) is fragile and prone to kinking, which can destroy the functionality of the guide wire. For this reason, surgeons are reluctant to remove the proximal connector from the guide wire during a procedure for fear of breaking the guide wire when reattaching the proximal connector. Having the guide wire coupled to the proximal connector further limits the maneuverability and handling of the guide wire.

Further, a problem with existing pressure and flow guide wires is that they require a complex assembly of many discrete components. That complex assembly process has limitations on design performance of the guide wire. The use of separate conductive wires running down the length of the wire reduces the space available for more supportive cores and can result in numerous issues during use due to poor solder joints with conductive bands, electrical shorts due to insulation issues, and breakage of the delicate conductive wires.

Accordingly, there remains a need for improved intravascular devices, systems, and methods that include one or more electronic, optical, or electro-optical components.

SUMMARY

The present disclosure is directed to intravascular devices, systems, and methods that include a guide wire having a core wire with embedded electrical conductors.

The present disclosure provides a more robust sensing guide wire that avoids the assembly and performance issues of prior sensing guide wires. Guide wires of the present disclosure have a core wire with one or more electrical conductors embedded therein. The electrical conductors extend the length of the core and act as the electrical pathway for sensor signals. The electrical conductors can be electrically isolated from the main body or primary material of the core wire by an insulating layer. The electrical conductors can be exposed by removing surrounding portions of the core wire (e.g., by grinding, etching, ablating, etc.) at specific locations on each conductor to facilitate the creation of electrical connections. In that regard, a proximal section of the conductor can be electrically coupled to a proximal connector (e.g., one or more conductive bands), while a distal section of the conductor can be electrically coupled to a sensing element. In that regard, the distal section of the conductor may be exposed for electrical connection as part of a distal shaping process. In this manner, guide wires of the present disclosure can eliminate the need for a hypotube and substantially reduce the need for adhesives and solder in formation of the guide wire. Reducing the number of components necessary to assemble the guide wires improves the robustness of the assembled guide wire by eliminating a multitude of processes and connection points that can create failure conditions.

Any type of sensor can be connected to guide wires of the present disclosure. In certain embodiments, only a single sensor is connected to the guide wire. In other embodiments, multiple sensors are connected to the guide wire. All of the sensors may be the same. Alternatively, the sensors may differ from each other and measure different characteristics inside a vessel. Exemplary sensors are pressure, flow, and temperature sensors. Generally, any type of pressure sensor may be used with the guide wires of the present disclosure, including piezoresistive, optical and/or combinations thereof. In certain embodiments, the pressure sensor includes a crystalline semi-conductor material. Similarly, any type of flow sensor may be used with guide wires of the present disclosure. In certain embodiments, the flow sensor includes an ultrasound transducer, such as a Doppler ultrasound transducer. The guide wire can include both a pressure sensor and a flow sensor.

Another aspect of the present disclosure provides methods for measuring a characteristic inside a vessel. The methods can include providing a sensing guide wire that includes a core wire with one or more embedded electrical conductors. The electrical conductors can be isolated from the main body of the core wire by an insulating layer. The conductive wires can be exposed at one or more locations along the core wire to facilitate electrical connection to a proximal connector and/or a sensing element. The guide wire is inserted into a vessel, and one or more sensing elements of the guide wire measure one or more characteristics inside the vessel.

The present disclosure provides intravascular devices that are stronger and more durable than existing designs, while also easier to manufacture. Embodiments of the present disclosure utilize a core member integrally embedded with one or more electrical conductors that facilitates the use of a larger core that provides better handling, strength, and durability than existing designs, which reduces the likelihood of unwanted bending, kinking, and/or other damage to the intravascular device that can be detrimental to the function of the device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 1 is a diagrammatic, schematic side view of an intravascular device according to an embodiment of the present disclosure.

FIG. 2 is a cross-sectional end view of the intravascular device of FIG. 1 taken along section line 2-2 according to an embodiment of the present disclosure.

DETAILED DESCRIPTION

Figure 3:
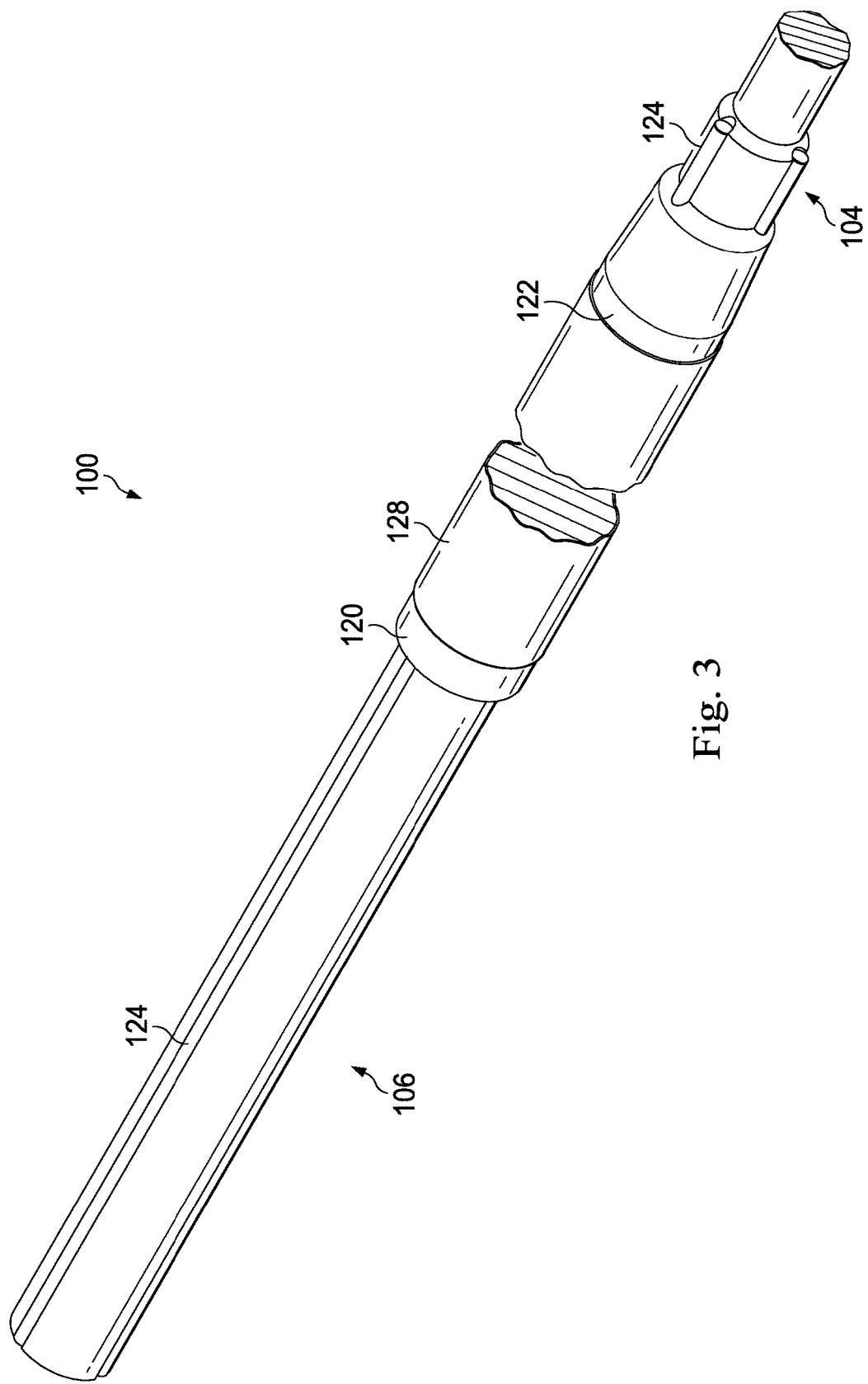
FIG. 3 is a diagrammatic perspective view of a core member of the intravascular device of FIGS. 1 and 2 according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. As discussed below, in some embodiments the electrical conductors are embedded within a core of the flexible elongate member. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Similarly, in some embodiments the optical fibers are embedded within a core of the flexible elongate member. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. In accordance with the present disclosure, at least one of the electrical conductors and/or optical pathways is embedded within the core of the flexible elongate member 102. Generally, any number of electrical conductors, optical pathways, and/or combinations thereof can extend along the length of the core of the flexible elongate member 102 between the connector 110 and the component 108. In some instances, between one and ten electrical conductors and/or optical pathways extend along the length of the core of the flexible elongate member 102 between the connector 110 and the component 108. The number of communication pathways and the number of electrical conductors and optical pathways extending along the length of the core of the flexible elongate member 102 is determined by the desired functionality of the component 108 and the corresponding elements that define component 108 to provide such functionality, the diameter of the flexible elongate member 102, and/or the diameter of the conductors and/or optical fibers.

Referring now to FIGS. 2-6, shown therein are aspects of the intravascular devices of the present disclosure that include communication pathways (e.g., electrical conductors and/or optical fibers) embedded within a core member and extending along the length of the device. In that regard, one of the major issues associated with existing functional guide wires is poor mechanical performance as compared to frontline guide wires. This performance loss is due in a large part to the typical design of the guide wires that severely limits the space available for the core or core wire due to the need to run the communication lines along the length of the device between the core wire and a surrounding hypotube. For the sake of clarity and simplicity, the embodiments described below include three electrical conductors embedded in a main core body, which may also be formed of a conductive material. Those skilled in the art will recognize that the concepts are applicable to intravascular devices that include virtually any number of electrical conductors and/or optical fibers extending along the length of the core wire. However, in most implementations the intravascular device will include between 1 and 10 communication pathways extending along the length of the core wire between a proximal portion and a distal portion of the intravascular device.

Referring more specifically to FIG. 2, a cross-sectional end view of the intravascular device 100 taken along section line 2-2 of FIG. 1. As shown, the flexible elongate member 102 is defined by a core member 120 according to an embodiment of the present disclosure. The core member 120 defines a main body having an outer surface 122. In some instances, the outer diameter of the core member 120 defined by the outer surface 122 is the same or substantially the same as the desired outer diameter of the intravascular device 100 that the core member 120 is intended to form. Accordingly, in some particular embodiments the outer diameter of the core member 120 is approximately 0.014", such as between 0.0138" and 0.0142". In some embodiments the outer diameter of the core member 120 is between about 0.0128" and about 0.0135" to allow for one or more outer coating layers.

As also shown in FIG. 2, the core member 120 includes conductors 124 embedded therein. In the illustrated embodiment, three conductors 124 are embedded within the main body of the core member 120. In that regard, the conductors 124 are fully encapsulated by the material forming the main body of the core member 120. In some embodiments, an insulating layer 126 is formed between the conductor 124 and the main body of the core member 120. To that end, the insulating layer 126 can be utilized to electrically isolate the conductor 124 from the main body of the core member 120. As a result, each of the conductors 124 and/or the main body of the core member 120 can be utilized as an independent electrical communication pathway of the intravascular device 100.

The core member 120 can be formed of any suitable material such as stainless steel, nickel and titanium alloys (such as Nitinol), polyetheretherketone, 304V stainless steel, MP35N, or other metallic or polymeric materials.

Each of the conductors 124 is formed of a conductive material, such as copper, gold, silver, platinum, or other suitable conductive material. Generally, the size of the conductors 124 is selected to allow the conductors 124 to be fully embedded within the material forming the core member 120, while still providing the appropriate conductive path for function of the component 108 of the intravascular device 100. Accordingly, in some instances the conductor is between a 24 AWG conductor and a 64 AWG conductor is utilized. In some instances, the conductor is between about 38 AWG and 52 AWG. 46 AWG and/or 48 AWG conductors are used in some implementations. The illustrated embodiment shows the conductors 124 being 46 AWG conductors. In other instances, larger or smaller conductors 124 are utilized. In certain embodiments, the conductors 124 are space substantially equally around a circumference of the main body of the core member 120. However, the conductors 124 may be embedded in any suitable manner and/or pattern, including symmetric, non-symmetric, geometric, and non-geometric patterns.

As noted above, the insulating layer 126 serves to electrically isolate the core member 120 from the conductors 124 and to isolate the conductors from one another. The insulating layer 126 may be formed of any suitable material. In some instances, the insulating layer is a polymer layer. Generally, the insulating layer 126 may have any suitable thickness, but in some instances has a thickness between about 0.0001" and about 0.001". In the illustrated embodiment, the insulating layer is shown as having a thickness of approximately 0.00025". In some instances, the conductors 124 are coated with the insulating layer 126 prior to being embedded within the main body of the core member 120. That is, an insulated conductor is provided separately and then embedded within the core member 120 during formation of the core member. In other instances, the main body of the core member 120, the insulating layer 126, and conductors 124 are formed as part of an integrated process of forming the core member 120.

In some embodiments, additional conductors and/or other elements of the intravascular device are secured and/or wrapped around the core member 120. For example, in some instances techniques such as those disclosed in U.S. patent application Ser. No. 14/143,304, filed Dec. 30, 2013, which is hereby incorporated by reference in its entirety.

Referring now to FIG. 3, shown therein is diagrammatic perspective view of the core member 120 according to an embodiment of the present disclosure. In that regard, the core member 120 is shown with the distal portion 104 and proximal portion 106 having been shaped for use in the intravascular device 100. In particular, the distal portion 104 has been shaped to expose the conductors 124 for electrical coupling to component 108, facilitate coupling to one or more flexible members and/or a sensor housing, facilitate physical coupling to the component 108, increase the flexibility of the distal tip of the intravascular device 102, and/or otherwise configure the characteristics of the distal portion of the intravascular device 102 for use.

In some embodiments, a coating 128 is provided on at least a portion of the outer surface 122 of the core member 120. In the illustrated embodiment, the coating 128 extends along a majority of the length of the core member 120 between the proximal portion 106 and the distal portion 104. The coating 128 can be a suitable hydrophilic or hydrophobic coating. In some implementations, the coating 128 provides increased lubricity to the core member 120. Exemplary coating materials include, without limitation, PTFE, PTFE impregnated polyimide, silicone-based coatings, and hydrophilic based coatings. Generally, the coating 128 will be a very thin layer of material. For example, in some implementations the coating 128 has a thickness less than about 0.0005", less than about 0.0001", and/or less than about 0.00005".

Figure 4:
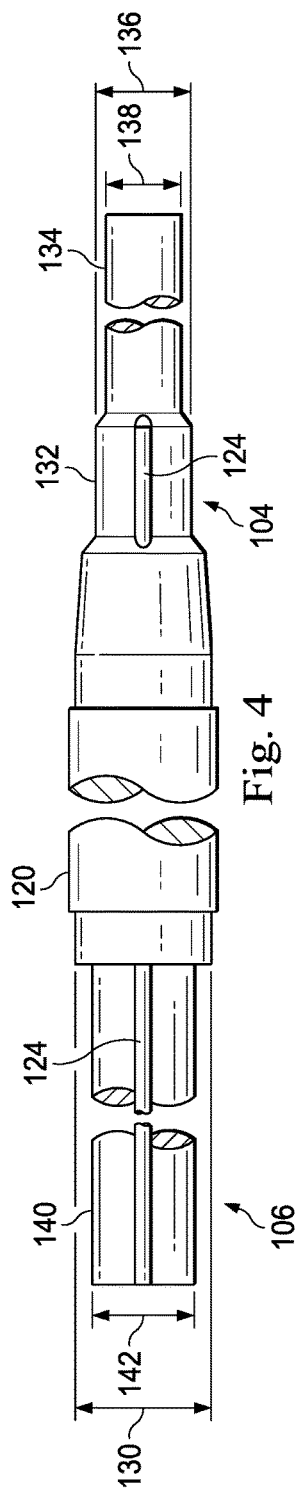
FIG. 4 is a diagrammatic, schematic side view of the core member of FIG. 3 according to an embodiment of the present disclosure.

Referring now to FIG. 4, shown therein is a diagrammatic, schematic side view of the core member 120 of FIG. 3. As shown the main body of the core member 120 has a diameter 130. Generally, the diameter 130 is approximately equal to the maximum desired outer diameter of the intravascular device 100 with room left for lubricious coating. Accordingly, in some particular implementations the diameter 130 is about 0.013", 0.017", or 0.034". As shown, the distal portion 104 of the core member 120 has been processed to include a portion 132 extending distally from the main body of the core member 120 and a portion 134 extended distally from portion 132. In some instances, the portions 132/134 are defined by grinding, etching, ablating, and/or otherwise removing surrounding portions of the core member 120.

In the illustrated embodiment, section 132 has a diameter 136 that is reduced relative to diameter 130 of the main body. In particular, in section 132 the outer portions of the core member 120 have been removed to expose the embedded conductors 124. By exposing the conductors 124, the component 108 can be electrically coupled to the conductors 124 (e.g., using solder, leads, additional conductors (insulated in some instances). Accordingly, in some instances, the diameter 136 of section 132 is between about 30% and about 90% of the diameter 130, with some particular embodiments being between about 70% and about 80% of the diameter 130. Accordingly, in some implementations, the diameter 136 of section 132 is between about 0.005" and about 0.012" for a 0.014" outer diameter intravascular device, with 0.010" being utilized in some particular embodiments; between about 0.005" and about 0.016" for a 0.018" outer diameter intravascular device, with 0.010" being utilized in some particular embodiments; and between about 0.005" and about 0.032" for a 0.035" outer diameter intravascular device, with 0.031" being utilized in some particular embodiments.

In the illustrated embodiment, section 134 has a diameter 138 that is reduced relative to diameter 136 of section 132. In particular, in section 134 the outer portions of the core member 120, including the embedded conductors 124, have been removed to reduce the stiffness and increase the flexibility of the core member 120. Accordingly, in some instances, the diameter 138 of section 134 is between about 10% and about 80% of the diameter 130, with some particular embodiments being between about 30% and about 60% of the diameter 130. Accordingly, in some implementations, the diameter 138 of section 134 is between about 0.001" and about 0.005" for a 0.014" outer diameter intravascular device, with 0.002" being utilized in some particular embodiments; between about 0.001" and about 0.008" for a 0.018" outer diameter intravascular device, with 0.003" being utilized in some particular embodiments; and between about 0.0025" and about 0.010" for a 0.035" outer diameter intravascular device, with 0.007" being utilized in some particular embodiments.

In some instances, section 134 and/or section 132 are shaped in a manner to facilitate coupling to additional elements of the intravascular device 100, including component 108, a housing for component 108, flexible members (coils, polymer tubes, and/or coil-embedded polymer tubes), and/or combinations thereof. In that regard, while the sections 132 and 134 are shown as having a constant diameter, in other instances the sections 132 and 134 include tapers, recesses, projections, and/or other structural features to facilitate coupling to other elements. In some particular instances, the core member 120 is coupled to a distal section, intermediate section, and/or proximal section similar to those described in one or more of U.S. Pat. Nos. 5,125,137, 5,873,835, 6,106,476, 6,551,250, and U.S. patent application Ser. No. 13/931,052 published as U.S. Patent Application Publication No. 2014/0005543 on Jan. 2, 2014, U.S. patent application Ser. No. 14/143,304 published as U.S. Patent Application Publication No. 2014/0187874 on Jul. 3, 2014, each of which is hereby incorporated by reference in its entirety. In that regard, the component 108 can be mounted within a distal section of the intravascular device 100 using any suitable technique, including without limitation those disclosed in one or more of U.S. Pat. No. 5,125,137, 5,873,835, 6,106,476, 6,551,250, U.S. patent application Ser. No. 13/931,052, published as U.S. Patent Application Publication No. 2014/0005543 on Jan. 2, 2014, U.S. patent application Ser. No. 14/135,117 published as U.S. Patent Application Publication No. 2014/0180141 on Jun. 26, 2014, U.S. patent application Ser. No. 14/137,364, published as U.S. Patent Application Publication No. 2014/0187980 on Jul. 3, 2014, and U.S. patent application Ser. No. 14/139,543, published as U.S. Patent Application Publication No. 2014/0187984 on Jul. 3, 2014, each of which is hereby incorporated by reference in its entirety.

In some implementations, the conductors 124 are exposed for electrical coupling to component 108 at an end surface extending perpendicular to the longitudinal axis of the core member 120. That is, the conductors 124 are not exposed along the length of the core member 120 (as shown in FIG. 4), but rather are exposed at an end surface of the core member 120 (similar to what is shown in FIG. 2), which may occur at intermediate transition point(s), such as the end of main body or end of section 132 and/or an end of the core member. In such instances, reduced diameter section(s) 106 and/or 132 may be omitted. For example, where the core member 120 is utilized as a drive cable in an intravascular ultrasound (IVUS) device, these reduced diameter section(s) may be eliminated.

As shown, the proximal portion 106 of the core member 120 has been processed to include a portion 140 extending proximally from the main body of the core member 120. In some instances, the portion 140 is defined by grinding, etching, ablating, and/or otherwise removing surrounding portions of the core member 120. In the illustrated embodiment, section 140 has a diameter 142 that is reduced relative to diameter 130 of the main body. In particular, in section 140 the outer portions of the core member 120 have been removed to expose the embedded conductors 124. By exposing the conductors 124, one or more connectors can be electrically coupled to the conductors 124 (e.g., using solder, leads, additional conductors (insulated in some instances) to define connector 110 of the intravascular device 100. As a result, the diameter 142 of section 140 can be the same as the diameter 136 of section 132 in some instances. Accordingly, in some implementations, the diameter 142 of section 140 is between about 0.005" and about 0.012" for a 0.014" outer diameter intravascular device, with 0.010" being utilized in some particular embodiments; between about 0.005" and about 0.016" for a 0.018" outer diameter intravascular device, with 0.010" being utilized in some particular embodiments; and between about 0.005" and about 0.032" for a 0.035" outer diameter intravascular device, with 0.031" being utilized in some particular embodiments.

Figure 5:
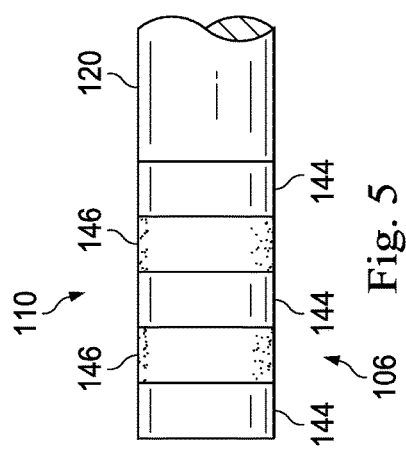
FIG. 5 is a diagrammatic, schematic side view of a proximal portion of an intravascular device according to an embodiment of the present disclosure.

Referring now to FIG. 5, shown therein is the proximal portion 106 of the intravascular device 100 formed over the core member 120 of FIGS. 3 and 4 according to an embodiment of the present disclosure. As shown, three conductive bands 144 are separated by insulators 146 to define connector 110 of the intravascular device 100. In some instances, the conductive bands 144 are printed onto the core member 120 by electrically printing or plating of a conductive material over the exposed portions of the conductors 124. In that regard, the conductive bands 144 are formed such that they have a uniform outer diameter matching the desired outer diameter of the intravascular device and/or the outer diameter of connector in some implementations. To facilitate formation of each of the conductive bands 144 in an electrically isolated manner relative to the other conductors 124, the embedded conductors 124 are exposed and then coated with an insulator material, such as polyimide. Then each individual conductor 124 is exposed (e.g., via laser ablation) at staggered locations along the length of the core member 120 that represent where the conductive bands 144 will be formed. In this manner, each conductive band 144 is electrically coupled to a single conductor 124 and electrically isolated from the remaining conductors 124. If desired, it is possible to electrically couple a conductive band 144 to more than one of the conductors 124.

Any desired pattern of conductive material may be placed onto the core member 120 to define the conductive bands 144. For example, the conductive bands 144 can be solid, multiple rings, a spiral, and/or any other pattern that provides the optimum functionality. In some instances, the conductive bands 144 are preformed cylindrical members that are positioned over the corresponding exposed sections of the conductors 124 and electrically coupled to the conductors using solder or other suitable techniques. In some embodiments, the conductive bands are swaged and/or laser welded in place. The insulating material utilized for insulators 146 may be any suitable insulating material.

In the illustrated embodiment, each of the three conductive bands 144 is electrically coupled to a single one of the conductors 124 and electrically isolated from the others (e.g., by one or more insulating layers). In some instances, the conductors 124 are exposed from the core member 120 only in locations along the length of the core member where the conductor 124 is to be coupled to the conductive band. A reference ring may be formed at a proximal or distal end of the core member 120 to determine where the conductors 124 are positioned relative to the circumference/outer surface of the core member 120 to facilitate selective exposure of only portions of the conductors 124. Those skilled in the art will recognize that there are numerous ways for electrically coupling the conductive bands 144 to the conductors 124 in an isolated manner. Further, it should be noted that in some instances an additional conductive band is provided and electrically coupled to the core member 120. In yet other instances, a portion of the core member 120 itself defines a conductive band.

Figure 6:
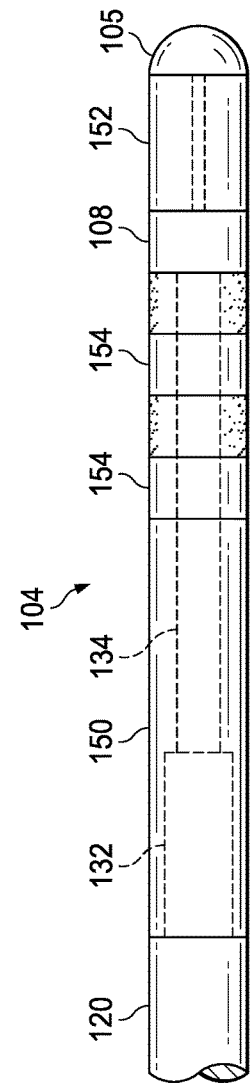
FIG. 6 is a diagrammatic, schematic side view of a distal portion of an intravascular device according to an embodiment of the present disclosure.

Referring now to FIG. 6, shown therein is the distal portion 104 of the intravascular device 100 formed over the core member 120 of FIGS. 3 and 4 according to an embodiment of the present disclosure. As shown, the distal portion 104 includes a flexible element 150 extending from the main body of the core member 120 over sections 132 and 134 to the component 108 (or a housing containing component 108). In that regard, the flexible element 150 may be a coil, a polymer tubing, and/or a coil-embedded polymer tubing. The distal portion 104 also includes a flexible element 152 extending distally from the component 108 (or a housing containing component 108) to the distal tip 105 of the intravascular device 100. Again, the flexible element 152 may be a coil, a polymer tubing, and/or a coil-embedded polymer tubing. In some instances, the flexible element 152 is radiopaque and/or includes a radiopaque tip. In some implementations, a flow sensor is positioned at the distal tip 105 of the intravascular device 100. Generally, the distal portion 104 of the intravascular device 100 may include features similar to those described in any of the patents and applications incorporated by reference above, but utilizing the core member 120 of the present disclosure having embedded conductors 124 as the core wire of the intravascular device.

As also shown in FIG. 6, the distal portion 104 can include one or more radiopaque markers 154. In that regard, the radiopaque markers 154 can be utilized to facilitate co-registration of the measurements obtained with the intravascular device 100 to corresponding images of the vessel, including angiography, x-ray, CT scans, IVUS, OCT, and/or other imaging modalities. In some implementations, co-registration is performed as disclosed in one or more of U.S. Pat. No. 7,930,014, U.S. patent application Ser. No. 14/144,280, published as U.S. Patent Application Publication No. 2014/0187920 on Jul. 3, 2014, U.S. patent application Ser. No. 14/335,603 published as U.S. Patent Application Publication No. 2014/0025330 on Jan. 22, 2015, and U.S. Provisional Patent Application No. 61/895,909 filed Oct. 25, 2013 titled "DEVICES, SYSTEMS, AND METHODS FOR VESSEL ASSESSMENT", each of which is hereby incorporated by reference in its entirety.

The radiopaque markers 154 can be formed of any radiopaque material. In some instances, the radiopaque markers 154 are coils formed of a radiopaque material. There may be any number of radiopaque markers 154, including one, two (as shown), three, or more. In some implementations, the radiopaque markers 154 are located proximal of the component 108 and its associated housing, if any. Further, in some instances the radiopaque markers 154 are elongated such that they have a greater length than typical balloon or stent markers, to allow the radiopaque markers 154 of the intravascular device 100 to be distinguished from the markers of other elements that may be positioned in the same region of the vessel. In some instances, the radiopaque markers 154 have a length along the longitudinal axis of the intravascular device 100 of between about 3 mm and about 10 mm, with some particular implementations having a length of about 5 mm.

As discussed above with respect to component 108, the sensor(s) of the intravascular device 100 provide a mechanism to obtain intraluminal measurements within a body lumen and are connected to the one or more conductive bands on the intravascular device, which transmit and receive signals from the sensor(s). For example, the guide wire of the present disclosure can include a pressure sensor, a flow sensor, a temperature sensor or combinations thereof. The guide wire can be a combination guide wire that includes both a pressure sensor and a flow sensor. Pressure sensors can be used to measure pressure within the lumen and flow sensors can be used to measure the velocity of blood flow. Temperature sensors can measure the temperature of a lumen. A guide wire with both a pressure sensor and a flow sensor provides a desirable environment in which to calculate fractional flow reserve (FFR) or other pressure ratio calculations using pressure readings, and coronary flow reserve (CFR) using flow readings. Guide wires with two or more sensors can be made by increasing the number of conductive wires embedded within the core member. In addition, the core member 120 may also be utilized as a conductor in some embodiments. Such embodiments provide enough conductive pathways to facilitate the use of at least two sensors with the intravascular device 100.

The ability to measure and compare both the pressure and velocity flow and create an index of hyperemic stenosis resistance significantly improves the diagnostic accuracy of this ischemic testing. It has been shown that distal pressure and velocity measurements, particularly regarding the pressure drop-velocity relationship such as Fractional Flow reserve (FFR), Coronary flow reserve (CFR) and combined P-V curves, reveal information about the stenosis severity. For example, in use, the guide wire may be advanced to a location on the distal side of the stenosis. The pressure and flow velocity may then be measured at a first flow state.

Then, the flow rate may be significantly increased, for example by the use of drugs such as adenosine, and the pressure and flow measured in this second, hyperemic, flow state. The pressure and flow relationships at these two flow states are then compared to assess the severity of the stenosis and provide improved guidance for any coronary interventions. The ability to take the pressure and flow measurements at the same location and same time with the combination tip sensor, improves the accuracy of these pressure-velocity loops and therefore improves the accuracy of the diagnostic information.

A pressure sensor can be mounted, for example, on a distal portion of the guide wire. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires of the senor are connected to a conductive band in the guide wire. Additional details of suitable pressure sensors that may be used with devices of the present disclosure are described in U.S. Pat. Nos. 6,106,476. 6,106,476 also describes suitable methods for coupling the pressure sensor to a guide wire. Those methods are applicable to coupling the sensor to the conductive bands in guide wires of the present disclosure.

In certain aspects, the guide wire of the present disclosure includes a flow sensor. The flow sensor can be used to measure blood flow velocity within the vessel, which can be used to assess coronary flow reserve (CFR). The flow sensor can be, for example, an ultrasound transducer, a Doppler flow sensor or any other suitable flow sensor, disposed at or in close proximity to the distal tip of the guide wire. The ultrasound transducer may be any suitable transducer, and may be mounted in the distal end using any conventional method, including the manner described in U.S. Pat. Nos. 5,125,137, 6,551,250 and 5,873,835.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
   a flexible elongate member sized and shaped to be inserted into a blood vessel of a patient, wherein the flexible elongate member comprises a core wire having a solid cross section, a proximal portion, a distal portion, and a main body extending between the proximal portion and the distal portion;
   a sensing element disposed at the distal portion of the flexible elongate member and configured to measure a characteristic associated with the blood vessel while positioned inside the blood vessel; and
   at least two non-coaxial electrical conductors in communication with the sensing element, wherein the at least two non-coaxial electrical conductors are spaced apart from one another and extend from the proximal portion to the distal portion,
   wherein, in the main body, the at least two non-coaxial electrical conductors are completely disposed within the solid cross section of the core wire, and
   wherein, at the proximal portion and the distal portion, the at least two non-coaxial electrical conductors are exposed.

2. The sensing guide wire of claim 1, further comprising a lubricating coating over the core wire along a majority of a length between the proximal portion and the distal portion.

3. The sensing guide wire of claim 1, wherein, at the proximal portion, the at least two non-coaxial electrical conductors are exposed at staggered longitudinal positions.

4. The sensing guide wire of claim 1, wherein the sensing element comprises at least one of a pressure sensor, a flow sensor, a temperature sensor, or a combination thereof.

5. The sensing guide wire of claim 1, further comprising a first flexible element extending from the main body, over the distal portion, to the sensing element.

6. The sensing guide wire of claim 5, wherein the first flexible element comprises at least one of a coil, a polymer tubing, or a coil embedded polymer tubing.

7. The sensing guide wire of claim 5, further comprising a second flexible element extending distally from the sensing element.

8. The sensing guide wire of claim 7, wherein the second flexible element comprises at least one of a coil, a polymer tubing, or a coil embedded polymer tubing.

9. The sensing guide wire of claim 7, wherein the second flexible element comprises a radiopaque tip.

10. The sensing guide wire of claim 7, wherein the second flexible element is radiopaque.

11. The sensing guide wire of claim 1,
    wherein the proximal portion of the core wire comprises a first diameter,
    wherein the main body of the core wire comprises a second diameter greater than the first diameter, and
    wherein the distal portion of the core wire comprises a third diameter smaller than the second diameter.

12. The sensing guide wire of claim 11, wherein the first diameter and the third diameter are between about 30% and about 90% of the second diameter.

13. The sensing guide wire of claim 11, wherein the second diameter is between about 0.013" and about 0.034".

14. The sensing guide wire of claim 11, wherein the first diameter and the third diameter are between 0.005" and about 0.032".

15. The sensing guide wire of claim 11,
    wherein the distal portion of the core wire further comprises a first distal portion and a second distal portion distal to the first distal portion, and wherein the first distal portion comprises the third diameter and the second distal portion comprises a fourth diameter smaller than the third diameter.

16. The sensing guide wire of claim 15, wherein the fourth diameter is between about 10% and about 80% of the second diameter.

17. The sensing guide wire of claim 1, wherein the core wire comprises a metal.

18. The sensing guide wire of claim 1, wherein the core wire comprises a solid cylindrical body.

* * * * *